United States Patent
Morita (10) Patent No.: US 8,786,955 B2
(45) Date of Patent: Jul. 22, 2014

(54) ENDOSCOPE OBJECTIVE OPTICAL SYSTEM

(71) Applicant: Olympus Medical Systems Corp., Tokyo (JP)

(72) Inventor: Kazuo Morita, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/050,796

(22) Filed: Oct. 10, 2013

(65) Prior Publication Data
US 2014/0098429 A1 Apr. 10, 2014

Related U.S. Application Data

(63) Continuation of application No. PCT/JP2013/063612, filed on May 15, 2013.

(30) Foreign Application Priority Data

May 17, 2012 (JP) .................................. 2012-113342

(51) Int. Cl.
| | |
|---|---|
| *G02B 13/04* | (2006.01) |
| *A61B 1/00* | (2006.01) |
| *G02B 23/26* | (2006.01) |
| *G02B 23/24* | (2006.01) |
| *A61B 1/05* | (2006.01) |

(52) U.S. Cl.
CPC ............. *G02B 23/243* (2013.01); *A61B 1/00* (2013.01); *A61B 1/00163* (2013.01); *A61B 1/051* (2013.01)
USPC ........................... 359/661; 600/101; 600/176

(58) Field of Classification Search
CPC .... G02B 23/243; A61B 1/00; A61B 1/00163; A61B 1/051
USPC .......................... 359/661, 753; 600/101, 176
See application file for complete search history.

(56) References Cited

U.S. PATENT DOCUMENTS

| | | | | |
|---|---|---|---|---|
| 4,979,808 A | * | 12/1990 | Yamagata et al. | 359/740 |
| 6,695,775 B2 | * | 2/2004 | Watanabe et al. | 600/176 |
| 7,027,231 B2 | * | 4/2006 | Miyano | 359/661 |
| 8,243,129 B2 | * | 8/2012 | Uzawa | 348/65 |
| 8,300,325 B2 | * | 10/2012 | Katahira | 359/770 |
| 8,477,436 B2 | * | 7/2013 | Sasamoto | 359/793 |

FOREIGN PATENT DOCUMENTS

JP   10-197787   7/1998

OTHER PUBLICATIONS

International Search Report, dated Jun. 18, 2013, issued in corresponding International Application No. PCT/JP2013/063612.

* cited by examiner

*Primary Examiner* — David N Spector
(74) *Attorney, Agent, or Firm* — Kenyon & Kenyon LLP (57) ABSTRACT

The diameter of an endoscope insertion portion is reduced, and a wide field angle of an endoscope insertion portion is obtained. An endoscope objective optical system includes, from an object side, a first lens formed of a plano-concave lens having a concave surface facing an image side, a second lens formed of a plano-concave lens having a concave surface facing the object side, an aperture stop, and a third lens formed of a plano-convex lens having a plane surface facing the object side, and satisfies $0.7 \leq |fab/f| 0.9$ $1.7 \leq |fe/fab| \leq 2$ $2 \leq fb/fa \leq 4$ where f: focal length of the entire system; fa: focal length of the first lens; fb: focal length of the second lens; fe: represents focal length of the third lens; fab: combined focal length from the first lens to the second lens.

2 Claims, 7 Drawing Sheets

ENDOSCOPE OBJECTIVE OPTICAL SYSTEM

TECHNICAL FIELD

The present invention relates to an endoscope objective optical system.

BACKGROUND ART

Conventionally, in order to obtain a lens system suitable for use of a solid-state imaging element, it is known to use an objective optical system which has a long back focus and a small size and which provides improvements in optical performance, such as an improvement in color reproducibility and a satisfactory correction of the image field curvature (see, for example, PTL 1).

The objective optical system disclosed in PTL 1 is used for forming an object image on a solid-state imaging element arranged on a linear optical axis. Therefore, a prism, and the like, which bends the optical axis, does not need to be arranged between the objective optical system and the solid-state imaging element, and hence a certain length of back focus is sufficient for the formation of the object image.

CITATION LIST

Patent Literature

{PTL 1} Japanese Unexamined Patent Application, Publication No. Hei 10-197787

SUMMARY OF INVENTION

Technical Problem

However, in an ultra-thin video-scope type endoscope (whose insertion portion has an outer diameter of, for example, 3 mm), it is dimensionally difficult that a substrate with a solid-state imaging element mounted thereon is arranged perpendicularly to the linearly extending optical axis of the objective optical system. Therefore, it is necessary that the substrate is arranged in parallel with the optical axis of the objective optical system, and that the optical axis is bent by a prism arranged between the objective optical system and the imaging element. When such configuration is adopted, a sufficiently long back focus is needed in order to arrange the prism between objective optical system and the imaging element. Therefore, such configuration is difficult to be realized by the objective optical system disclosed in PTL 1.

The present invention has been made in view of the above described circumstances. An object of the present invention is to provide an endoscope objective optical system capable of reducing the diameter of an endoscope insertion portion and obtaining a wide field angle of the endoscope insertion portion.

Solution to Problem

In order to achieve the above described object, the present invention provides the following solutions.

An aspect of the present invention provides an endoscope objective optical system including, in order from an object side, a first lens formed of a plano-concave lens having a concave surface facing an image side, a second lens formed of a plano-concave lens having a concave surface facing the object side, an aperture stop, and a third lens formed of a plano-convex lens having a plane surface facing the object side, the endoscope objective optical system satisfying the following conditional expressions (1) to (3):

$$0.7 \leq |fab/f| \leq 0.9 \quad (1)$$

$$1.7 \leq |fe/fab| \leq 2 \quad (2)$$

$$2 \leq fb/fa \leq 4 \quad (3)$$

where f represents a focal length of the entire system, fa represents a focal length of the first lens, fb represents a focal length of the second lens, fe represents a focal length of the third lens, and fab represents a combined focal length from the first lens to the second lens.

According to the present aspect, when the endoscope objective optical system satisfies conditional expression (1), a long back focus can be obtained, and when the endoscope objective optical system satisfies conditional expression (2), a wide field angle can be obtained. Further, when the endoscope objective optical system satisfies conditional expression (3), the height of a light beam passing through the first lens can be suppressed low and thereby the diameter of the first lens can be reduced. That is, in the endoscope objective optical system which satisfies these three conditions (1) to (3), a long back focus can be obtained so that an imaging element can be arranged in parallel with the optical axis of the objective optical system and the optical axis can be bent by a prism. Also, the diameter of the endoscope objective optical system can be reduced so as to be applicable to an ultra-thin insertion portion, and the field angle of the endoscope objective optical system can be increased.

In the above-described aspect, the endoscope objective optical system may satisfy the following conditional expression (4):

$$0.9 \leq Na/Nb \leq 1 \quad (4)$$

where Na represents a refractive index at a d-line of a glass material forming the first lens, and Nb represents a refractive index at a d-line of a glass material forming the second lens.

With this configuration, the curvature of the second lens can be made large, as a result which the total thickness of the second lens can be reduced. Therefore, the distance from the first lens to the brightness diaphragm can be reduced, so that the height of the light beam passing through the first lens can be suppressed low and thereby the diameter of the first lens can be further reduced.

Advantageous Effects of Invention

According to the present invention, it is possible to obtain the effects that the diameter of an endoscope insertion portion is reduced and that a wide field angle of the endoscope insertion portion is obtained.

DESCRIPTION OF EMBODIMENT

In the following, an endoscope objective optical system 1 according to an embodiment of the present invention will be described with reference to the accompanying drawings.

Figure 1:
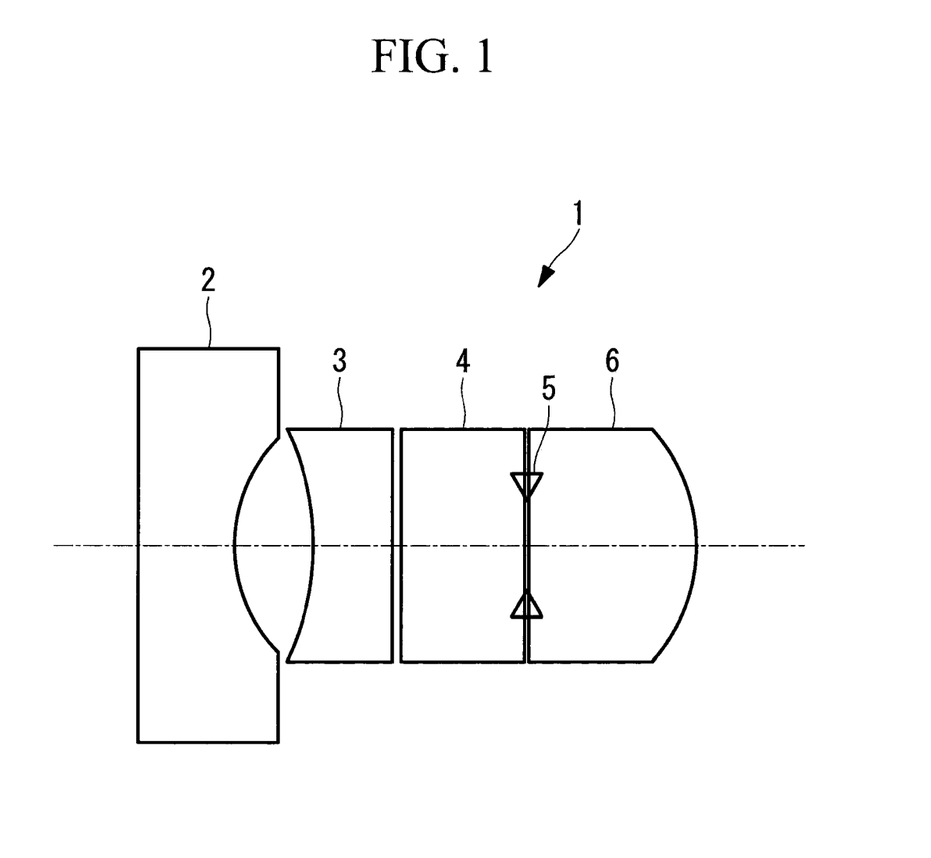
FIG. 1 is a view showing an endoscope objective optical system according to an embodiment of the present invention.

As shown in FIG. 1, the endoscope objective optical system 1 according to the present embodiment includes, in order from the object side, a first lens 2, a second lens 3, an infrared cut filter 4, an aperture stop 5, and a third lens 6.

The first lens 2 is a plano-concave lens and is arranged so that the concave surface thereof faces the image side.

The second lens 3 is a plano-concave lens and is arranged so that the concave surface thereof faces the object side.

The third lens 6 is a plano-convex lens and is arranged so that the plane surface thereof faces the object side.

In the present embodiment, each of the lenses 2, 3 and 6 satisfy the following conditional expressions (1) to (4).

$$0.7 \leq |fab/f| \leq 0.9 \quad (1)$$

$$1.7 \leq |fe/fab| \leq 2 \quad (2)$$

$$2 \leq fb/fa \leq 4 \quad (3)$$

$$0.9 \leq Na/Nb \leq 1 \quad (4)$$

Here, f represents the focal length of the entire system, fa represents the focal length of the first lens 2, fb represents the focal length of the second lens 3, fe represents the focal length of the third lens 6, fab represents the combined focal length from the first lens 2 to the second lens 3, Na represents a refractive index at a d-line of a glass material forming the first lens 2, and Nb represents a refractive index at a d-line of a glass material forming the second lens 3.

The effects of the endoscope objective optical system 1 according to the present embodiment configured in this way are described as follows.

In the endoscope objective optical system 1 according to the present embodiment, each of the first lens 2 and the second lens 3 is configured by a plano-concave lens, so that the negative power can be divided by the two lenses 2 and 3. Therefore, the negative power of each of the first lens 2 and the second lens 3 can be made smaller than the negative power at the time when the portion corresponding to the first and second lenses 2 and 3 is realized by using a single lens. As a result, ease of processing can be improved as compared with the case where a lens having a small diameter and strong negative power is processed.

Further, when the endoscope objective optical system 1 according to the present embodiment satisfies conditional expression (1), a long back focus can be obtained.

Figure 2:
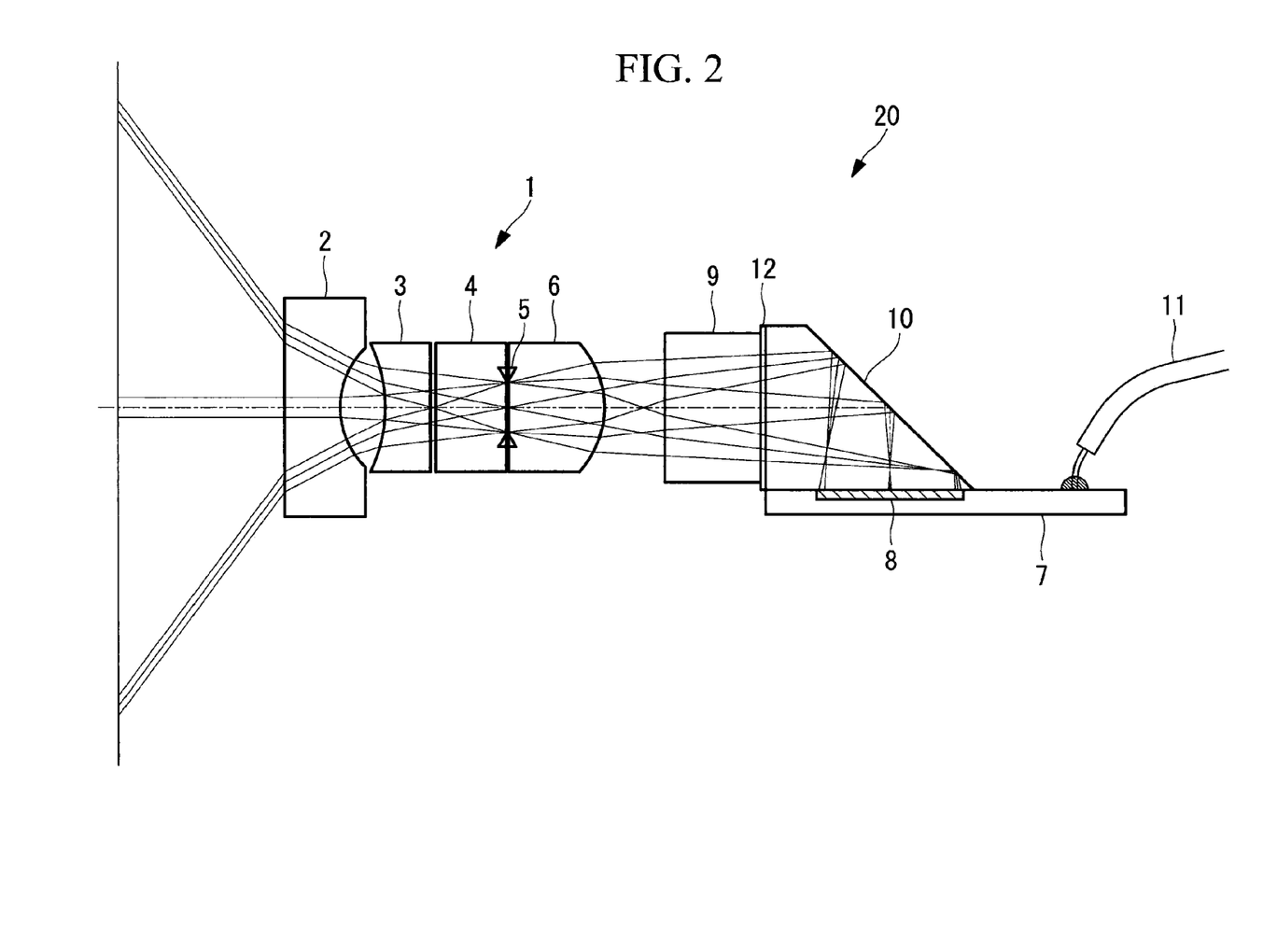
FIG. 2 is a view showing an imaging optical system including the endoscope objective optical system of FIG. 1.

That is, as shown in FIG. 2, the endoscope objective optical system 1 according to the present embodiment is used in such a manner that a substrate 7 is arranged in parallel with the optical axis of the endoscope objective optical system 1, and that a parallel plate 9 and a prism 10 are arranged between the endoscope objective optical system 1 and a solid-state imaging element 8 provided on the substrate 7.

The back focus length of the endoscope objective optical system 1 is increased to thereby enable the parallel plate 9 and the prism 10 to be arranged. Even with such arrangement, the size of the substrate 7 does not directly affect the size of the outer diameter of the insertion portion. Therefore, even when the size of the substrate 7 is large, the diameter of the insertion portion can be reduced. In FIG. 2, reference numeral 11 denotes a wiring connected to the substrate 7, and reference numeral 12 denotes an adhesive layer.

Further, when the endoscope objective optical system 1 according to the present embodiment satisfies conditional expression (2), a wide field angle can be obtained.

Further, when the endoscope objective optical system 1 according to the present embodiment satisfies conditional expression (3), the height of the light beam passing through the first lens 2 can be suppressed low. As a result, the outer diameter of the first lens 2 can be reduced, and thereby the outer diameter of the insertion portion can be reduced.

When the endoscope objective optical system 1 according to the present embodiment satisfies the above-described three conditions, the back focus can be made long enough to provide the prism 10, and the like. Therefore, the endoscope objective optical system 1 according to the present embodiment has advantages of reducing the diameter of the insertion portion and of increasing the field angle.

Further, when the endoscope objective optical system 1 according to the present embodiment satisfies conditional expression (4), the curvature of the second lens 3 can be kept large. As a result, the total thickness of the second lens 3 is made small, so that the distance from the first lens 2 to the brightness diaphragm 5 can be reduced. That is, the height of the light beam passing through the first lens 2 can be suppressed low also by this effect. As a result, the outer diameter of the first lens 2 can be made small, and thereby the diameter of the insertion portion can be further reduced.

Figure 3:
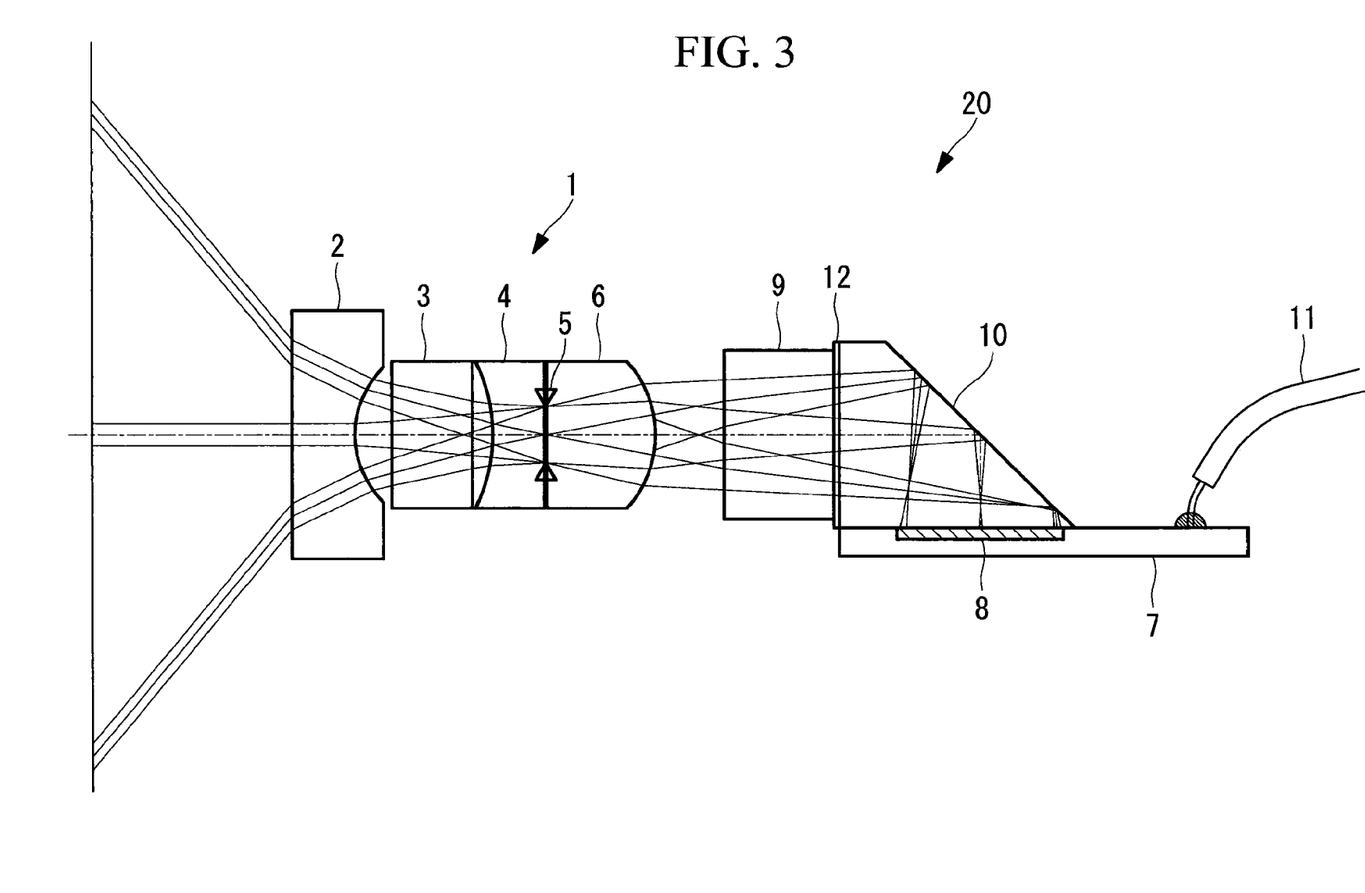
FIG. 3 is a view showing a modification of the endoscope objective optical system of FIG. 1.

It should be noted that, in the present embodiment, an example is shown in which the infrared cut filter 4 is arranged between the second lens 3 and the third lens 6, but instead of this arrangement, as shown in FIG. 3, the infrared cut filter 4 may be arranged between the first lens 2 and the second lens 3.

EXAMPLES

Next, examples of the endoscope objective optical system 1 according to the above-described embodiment will be described below.

First Example

Figure 4:
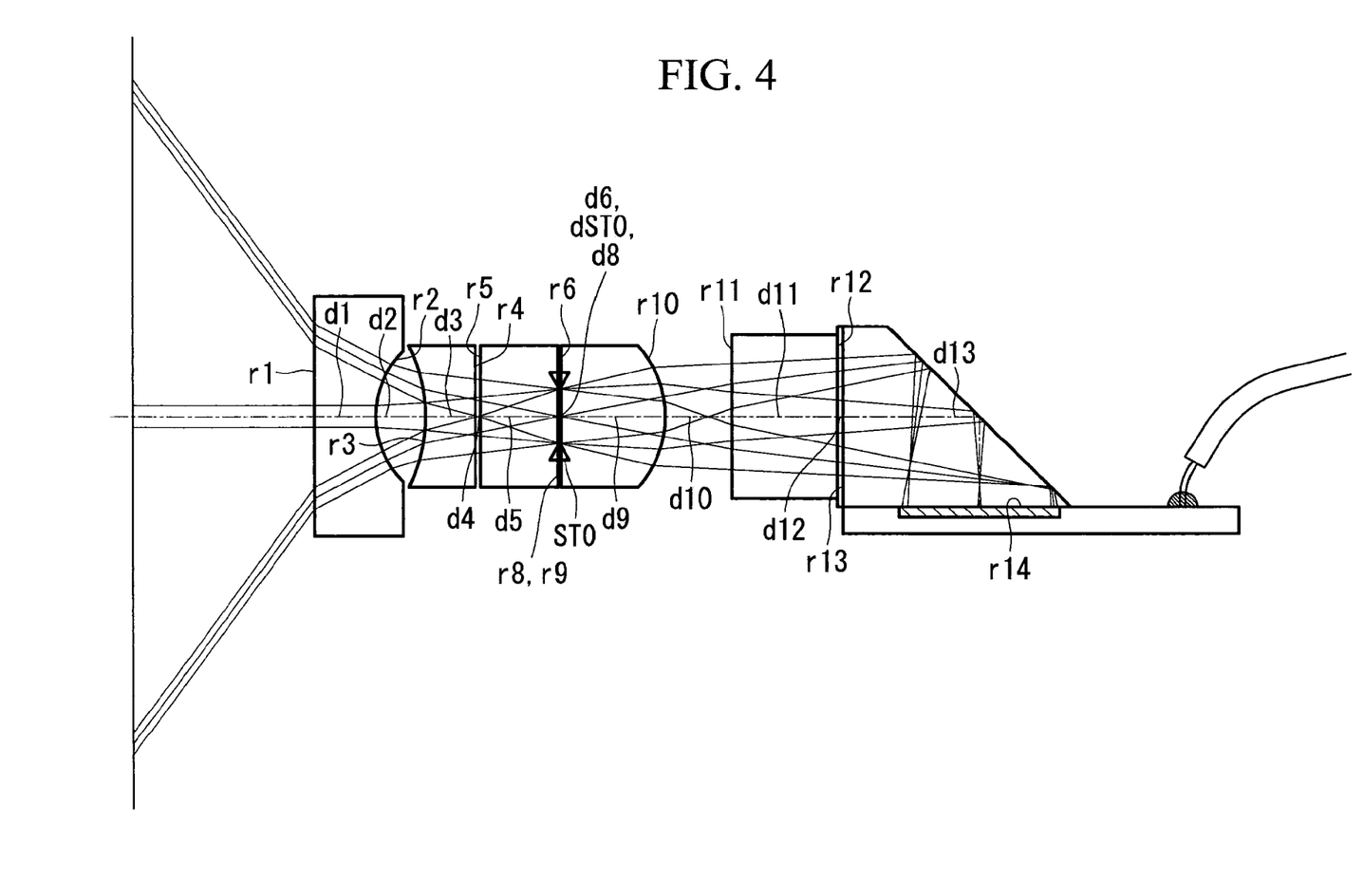
FIG. 4 is a view showing a lens array of an imaging optical system including a first example of the endoscope objective optical system of FIG. 1.

FIG. 4 shows a lens array of an imaging optical system 20 including the endoscope objective optical system 1, according to a first example of the present embodiment, and Table 1 shows lens data. The lens data of Table 1 are normalized so that the focal length of the entire system is substantially equal to 1.

In the present example, the field angle is set to 108°.

TABLE 1

| Surface number | r | d | n | ν |
|---|---|---|---|---|
| Object | ∞ | 56.577 | | |
| 1 | ∞ | 0.6506309 | 1.7682 | 71.79 |
| 2 | 1.001406 | 0.4813701 | | |
| 3 | −2.944812 | 0.6223426 | 1.882997 | 40.765107 |
| 4 | ∞ | 0.057 | | |
| 5 | ∞ | 0.848649 | 1.52113 | 66.5 |
| 6 | ∞ | 0 | | |
| STO | ∞ | 0.0282883 | | |
| 8 | ∞ | 0 | | |

TABLE 1-continued

| Surface number | r | d | n | ν |
|---|---|---|---|---|
| 9 | ∞ | 1.131532 | 1.882997 | 40.765107 |
| 10 | −1.306919 | 0.7358551 | | |
| 11 | ∞ | 1.131532 | 1.51633 | 64.142022 |
| 12 | ∞ | 0.0565766 | 1.51 | 64.14 |
| 13 | ∞ | 2.480884 | 1.61061 | 50.2 |
| 14 | ∞ | 0 | | |

Further, in the present example, the specification values of the lenses are as follows.

fab=−0.849
f=0.988
fa=−3.335
fb=−1.304
fe=1.48
Na=1.7682
Nb=1.882997

Second Example

Figure 5:
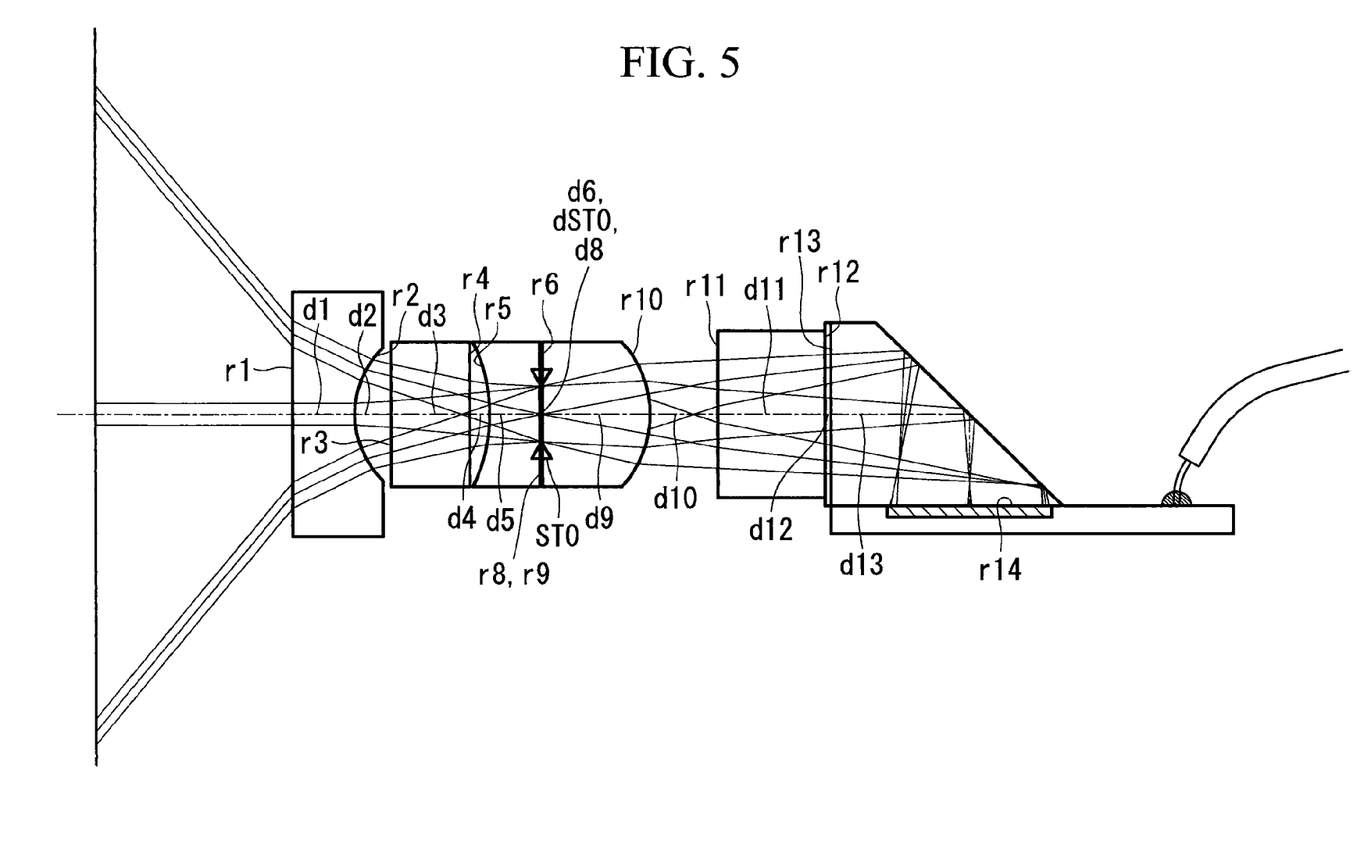
FIG. 5 is a view showing a lens array of an imaging optical system including a second example of the endoscope objective optical system of FIG. 1.

FIG. 5 shows a lens array of an imaging optical system 20 including the endoscope objective optical system 1, according to a second example of the present embodiment, and Table 2 shows lens data. The lens data of Table 2 are normalized so that the focal length of the entire system is substantially equal to 1.

In the present example, the field angle is set to 100°.

TABLE 2

| Surface number | r | d | n | ν |
|---|---|---|---|---|
| Object | ∞ | 53.855 | | |
| 1 | ∞ | 0.6193284 | 1.7682 | 71.79 |
| 2 | 0.9532272 | 0.373 | | |
| 3 | ∞ | 0.8078197 | 1.52113 | 66.5 |
| 4 | ∞ | 0.139 | | |
| 5 | −2.803134 | 0.5924011 | 1.882997 | 40.765107 |
| 6 | ∞ | 0 | | |
| STO | ∞ | 0.02692732 | | |
| 8 | ∞ | 0 | | |
| 9 | ∞ | 1.077093 | 1.882997 | 40.765107 |
| 10 | −1.14979 | 70.7054959 | | |
| 11 | ∞ | 1.077093 | 1.51633 | 64.142022 |
| 12 | ∞ | 0.05385465 | 1.51 | 64.14 |
| 13 | ∞ | 2.361526 | 1.61061 | 50.2 |
| 14 | ∞ | 0 | | |

Further, in the present example, the specification values of the lenses are as follows.

fab=−0.722
f=0.989
fa=−1.241
fb=−3.175
fe=1.302
Na=1.7682
Nb=1.882997

Third Example

Figure 6:
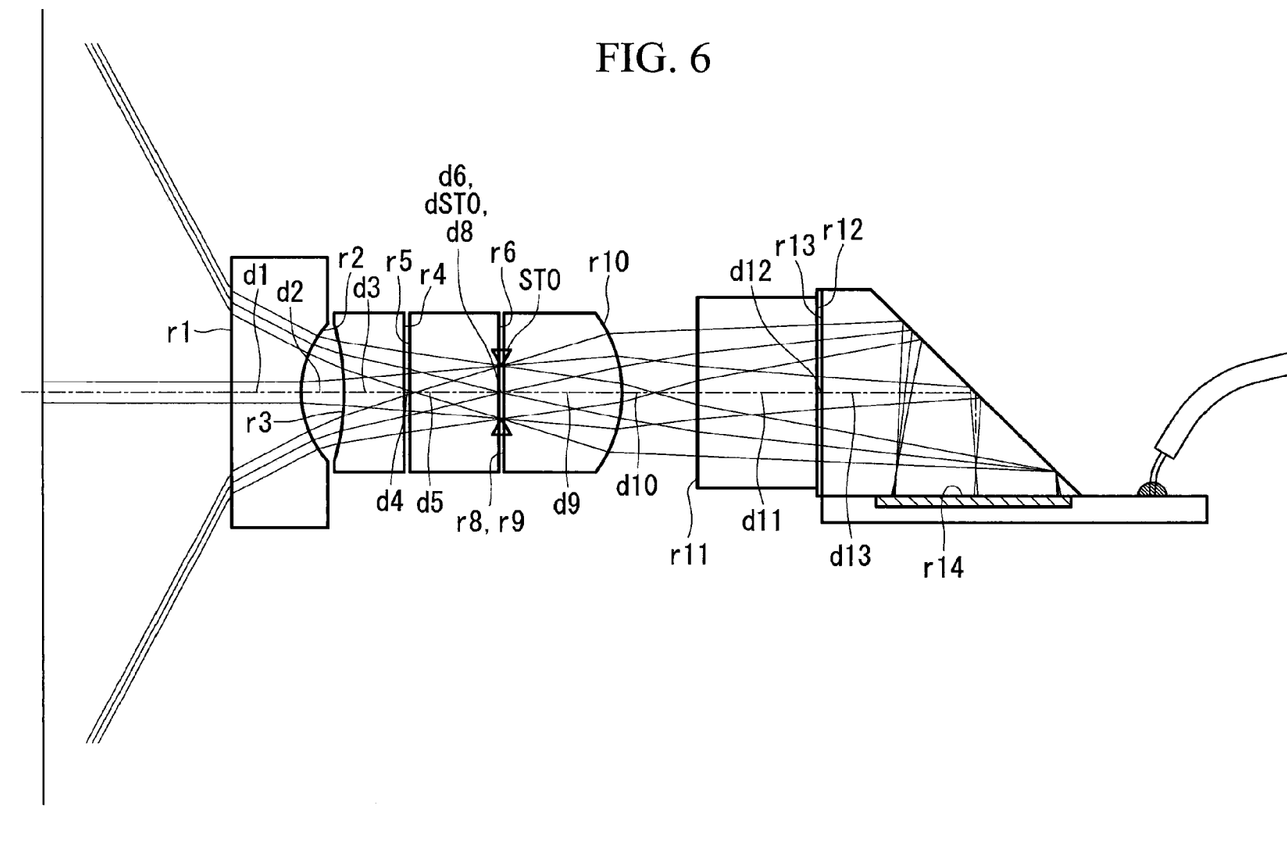
FIG. 6 is a view showing a lens array of an imaging optical system including a third example of the endoscope objective optical system of FIG. 1.

FIG. 6 shows a lens array of an imaging optical system 20 including the endoscope objective optical system 1, according to a third example of the present embodiment, and Table 3 shows lens data. The lens data of Table 3 are normalized so that the focal length of the entire system is substantially equal to 1.

In the present example, the field angle is set to 125°.

TABLE 3

| Surface number | r | d | n | ν |
|---|---|---|---|---|
| Object | ∞ | 62.893 | | |
| 1 | ∞ | 0.7232704 | 1.882997 | 40.765107 |
| 2 | 1 | 0.4865849 | | |
| 3 | −4.207973 | 0.6918239 | 1.92286 | 18.896912 |
| 4 | ∞ | 0.06289308 | | |
| 5 | ∞ | 0.9433962 | 1.52113 | 66.5 |
| 6 | ∞ | 0 | | |
| STO | ∞ | 0.06289308 | | |
| 8 | ∞ | 0 | | |
| 9 | ∞ | 1.259103 | 1.882997 | 40.765107 |
| 10 | −1.43547 | 0.8115168 | | |
| 11 | ∞ | 1.257862 | 1.51633 | 64.142022 |
| 12 | ∞ | 0.06289308 | 1.51 | 64.14 |
| 13 | ∞ | 2.757862 | 1.61061 | 50.2 |
| 14 | ∞ | 0 | | |

Further, in the present example, the specification values of the lenses are as follows.

fab=−0.829
f=0.999
fa=−1.126
fb=−4.504
fe=1.616
Na=1.882997
Nb=1.92286

Fourth Example

Figure 7:
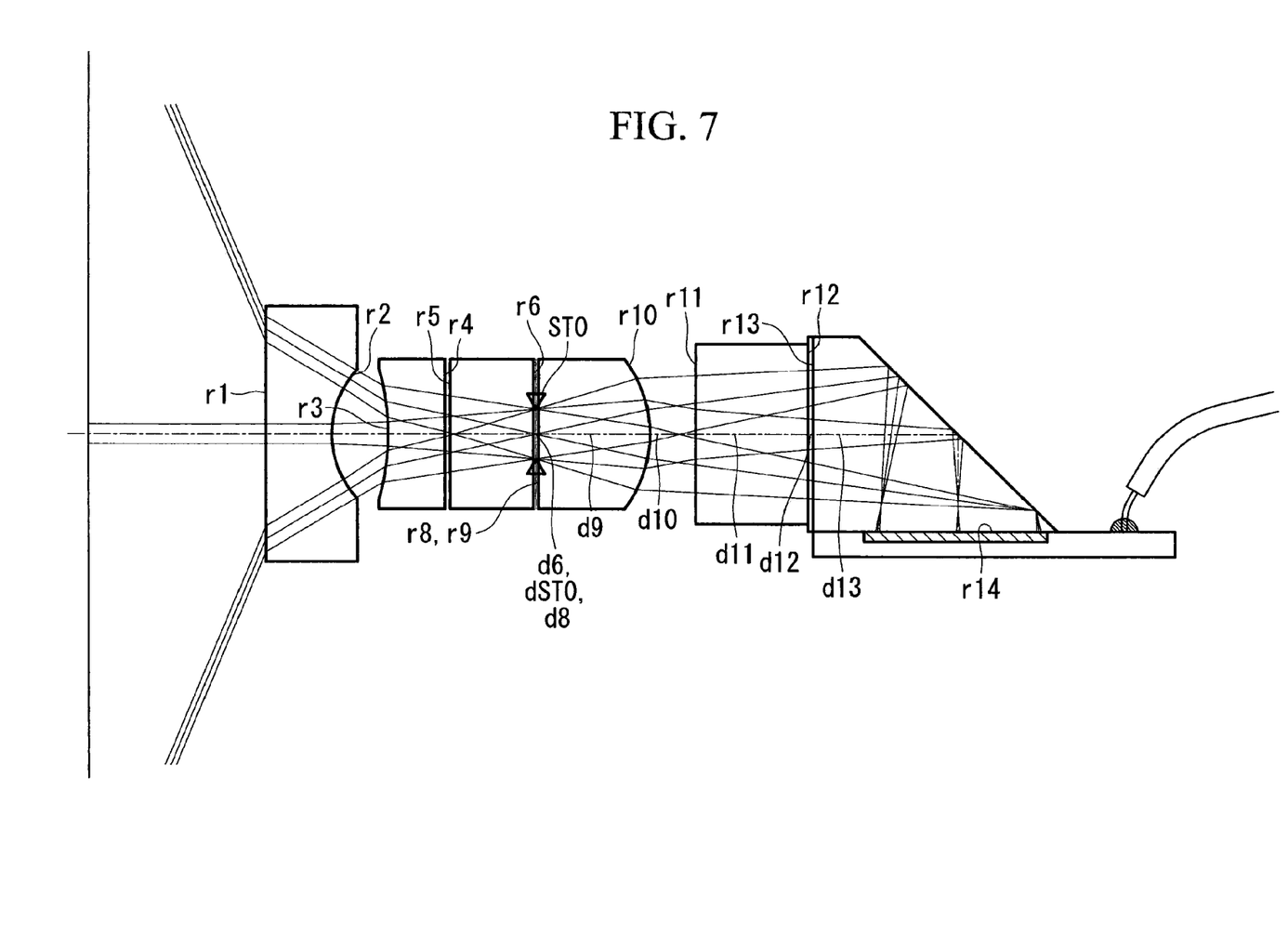
FIG. 7 is a view showing a lens array of an imaging optical system including a fourth example of the endoscope objective optical system of FIG. 1.

FIG. 7 shows a lens array of an imaging optical system 20 including the endoscope objective optical system 1, according to a fourth example of the present embodiment, and Table 4 shows lens data. The lens data of Table 4 are normalized so that the focal length of the entire system is substantially equal to 1.

In the present example, the field angle is set to 134°.

TABLE 4

| Surface number | r | d | n | ν |
|---|---|---|---|---|
| Object | ∞ | 62.893 | | |
| 1 | ∞ | 0.7232704 | 1.772499 | 49.598371 |
| 2 | 1.199298 | 0.6595863 | | |
| 3 | −2.887181 | 0.6918239 | 1.92286 | 18.896912 |
| 4 | ∞ | 0.06289308 | | |
| 5 | ∞ | 0.9433962 | 1.52113 | 66.5 |
| 6 | ∞ | 0 | | |
| STO | ∞ | 0.06289308 | | |
| 8 | ∞ | 0 | | |
| 9 | ∞ | 1.259103 | 1.882997 | 40.765107 |
| 10 | −1.42779 | 0.539 | | |
| 11 | ∞ | 1.257862 | 1.51633 | 64.142022 |
| 12 | ∞ | 0.06289308 | 1.51 | 64.14 |
| 13 | ∞ | 2.757862 | 1.61061 | 50.2 |
| 14 | ∞ | 0 | | |

Further, in the present example, the specification values of the lenses are as follows.

fab=−0.902
f=1.001
fa=−1.545
fb=−3.09
fe=1.608
Na=1.772499
Nb=1.92286

Table 5 shows values of conditional expressions (1) to (4) in the first to fourth examples.

From Table 5, it is seen that each of the first to fourth examples satisfies conditional expressions (1) to (4).

Further, Table 6 shows, as reference examples, values of conditional expressions (1) to (4) in each of the examples of PTL 1. It is seen that all of these examples do not satisfy conditional expressions (1) to (4).

TABLE 5

| CONDITIONAL EXPRESSION | FIRST EXAMPLE | SECOND EXAMPLE | THIRD EXAMPLE | FOURTH EXAMPLE |
|---|---|---|---|---|
| (1) | 0.85 | 0.72 | 0.83 | 0.90 |
| (2) | 1.74 | 1.80 | 1.95 | 1.78 |
| (3) | 2.56 | 2.56 | 4.00 | 2.00 |
| (4) | 0.94 | 0.94 | 0.98 | 0.90 |

TABLE 6

| CONDITIONAL EXPRESSION | FIRST EXAMPLE OF PRECEDING EXAMPLE | SECOND EXAMPLE OF PRECEDING EXAMPLE | THIRD EXAMPLE OF PRECEDING EXAMPLE | FOURTH EXAMPLE OF PRECEDING EXAMPLE |
|---|---|---|---|---|
| (1) | 1.392 | 1.335 | 1.334 | 4.854 |
| (2) | 0.84 | 0.953 | 0.953 | 0.277 |
| (3) | 0.964 | 1.524 | 1.524 | −2.629 |
| (4) | 1.244 | 1.244 | 1.244 | — |

{Reference Signs List}

| 1 | Endoscope objective optical system |
| 2 | First lens |
| 3 | Second lens |
| 5 | Brightness diaphragm |
| 6 | Third lens |

The invention claimed is:

1. An endoscope objective optical system comprising in order from an object side:
  a first lens formed of a plano-concave lens having a concave surface facing an image side;
  a second lens formed of a plano-concave lens having a concave surface facing the object side;
  an aperture stop; and
  a third lens formed of a plano-convex lens having a plane surface facing the object side,
  the endoscope objective optical system satisfying the following conditional expressions (1) to (3):

$$0.7 \leq |fab/f| \leq 0.9 \tag{1}$$

$$1.7 \leq |fe/fab| \leq 2 \tag{2}$$

$$2 \leq fb/fa \leq 4 \tag{3}$$

where f represents a focal length of the entire system,
  fa represents a focal length of the first lens,
  fb represents a focal length of the second lens,
  fe represents a focal length of the third lens, and
  fab represents a combined focal length from the first lens to the second lens.

2. The endoscope objective optical system according to claim 1, satisfying the following conditional expression (4):

$$0.9 \leq Na/Nb \leq 1 \tag{4}$$

where Na represents a refractive index at a d-line of a glass material forming the first lens, and
  Nb represents a refractive index at a d-line of a glass material forming the second lens.

* * * * *